United States Patent [19]

Horrom

[11] 3,998,971
[45] Dec. 21, 1976

[54] NOVEL N-VINYLOXYETHYL-α-METHYL-β-PHENETHYLAMINES FOR DEPRESSING APPETITE

[75] Inventor: Bruce Wayne Horrom, Waukegan, Ill.

[73] Assignee: Abbott Laboratories, North Chicago, Ill.

[22] Filed: Sept. 10, 1975

[21] Appl. No.: 611,951

Related U.S. Application Data

[60] Division of Ser. No. 498,013, Aug. 16, 1974, Pat. No. 3,925,475, which is a continuation-in-part of Ser. No. 481,626, June 21, 1974, abandoned.

[52] U.S. Cl. .............................................. 424/330
[51] Int. Cl.² ..................................... A61K 31/135
[58] Field of Search ................................... 424/330

*Primary Examiner*—Stanley J. Friedman
*Attorney, Agent, or Firm*—Gildo E. Fato; Robert L. Niblack

[57] ABSTRACT

Novel N-vinyloxyethyl-α-methyl-β-phenethylamines represented by the formula

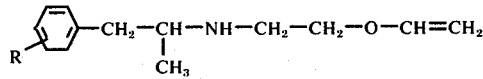

wherein R is H, halo or $CF_3$ and acid addition salts thereof. The compounds are useful as appetite depressants.

3 Claims, No Drawings

NOVEL N-VINYLOXYETHYL-α-METHYL-β-PHENETHYLAMINES FOR DEPRESSING APPETITE

This is a division, of application Ser. No. 498,013 filed Aug. 16, 1974 now U.S. Pat. No. 3925,475 which is in turn a Continuation-in-Part of U.S. Serial No. 481,626 filed June 21, 1974, now abandoned.

BACKGROUND OF THE INVENTION

Appetite suppressants commonly produce side effects such as acting as a stimulant. A relatively recently introduced appetite suppressant commonly known as fenfluramine and having the following formula:

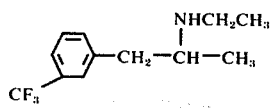   A acts as a sedative rather than a stimulant (Nursing 74, January, Pages 15 & 16). Reports indicate that fenfluramine, when given before meals, consistently reduced post absorption glucose levels in maturity onset, and insulin-requiring diabetics and unlike other hypoglycemic agents, it appears to improve glucose tolerance in diabetics without producing undersirable side effects, "Hypoglycemic Action of Fenfluramine in Diabetics Mellitus", J. R. Turtle et al., Diabetes, 22:858 – 867, November 1973.

DETAILED DESCRIPTION OF THE INVENTION

This invention relates to novel phenethylamines and more particularly relates to novel N-vinyloxyethyl-α-methyl-β-phenethylamines and acid addition salts thereof which are useful as appetite depressants.

The compounds of this invention are represented by the formula

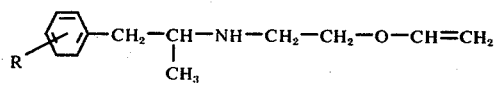   B wherein R is hydrogen, halo or trifluoromethyl and acid addition salts thereof.

The term "halo" as used herein, includes chloro, fluoro, bromo and iodo.

The compounds are useful as appetite depressants when administered orally to mammals in dosages of from 5 to 20 mg./kg. of body weight daily.

The preparation of the compounds of this invention is represented by the following reaction sequence:

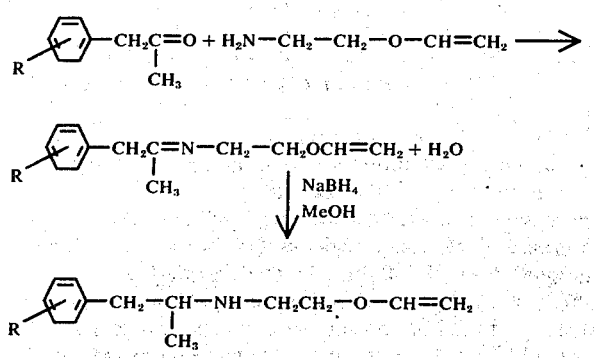

The starting materials can be prepared by methods well known in the art.

The following examples further illustrate the present invention:

EXAMPLE 1

N-(2-vinyloxyethyl)-α-methyl-β-phenylethylamine

A solution of 40.2 g. (0.3 mole) of phenylacetone, 26.2 g. (0.3 mole) of 2-aminoethyl vinyl ether and 200 cc. of anhydrous benzene were heated under reflux under a DeanStart water separator until the theoretical amount of water was removed (ca. 4 hours). At the end of this time, the benzene was removed under vacuum and the resulting crude imine was taken up in 450 cc. of dry methanol. To this solution was added 22.6 g. (0.6 mole) of sodium borohydride in small portions over a period of ½ hour. After the addition was complete, the reaction mixture was refluxed for 3 hours. The methanol was removed under vacuum and 300 cc. of water, 150 cc. of 20% potassium hydroxide and 60 g. of potassium hydroxide were added successively and the resulting oil was extracted with ether. After drying the ether solution over anhydrous magnesium sulfate, filtering and concentrating the resulting oil, it was distilled. 32.5 g. (64% yield) of the product as a colorless oil was obtained, b.p. 100°–102°/1.5 mm; $N_D^{25}$ 1.5070.

EXAMPLE 2

N-(2-vinyloxyethyl)-α-methyl-β-(4-chlorophenyl) ethyl amine was prepared from 4-chlorophenylacetone and 2-aminoethylvinyl ether according to the method of Example 1 to yield the product (58% yield) as a colorless oil, b.p. 103°–104°/0.4 mm; $N_D^{25}$ 1.5199.

EXAMPLE 3

N-(2-vinyloxyethyl)-α-methyl-β-(4-cholorophenyl) ethylamine hydrochloride

A solution of 12.0 g. (0.050 mole) amine in 50 ml. anhydrous ether was cooled in an ice bath. Then 28 ml. of an 1.2N solution of ethanol-HCl was added slowly. After cooling one hour in an ice bath, the product was collected by filtration and washed with anhydrous ether. Obtained 9.3 g. (67.5%), MP. 142°– 143°. The salt is soluble in water.

| Elemental Analysis | Calculated | Found |
|---|---|---|
| C | 56.53 | 56.38 |
| H | 6.93 | 7.23 |
| N | 5.07 | 5.09 |

EXAMPLE 4

N-(2-vinyloxyethyl)-α-methyl-β-(3-trifluoromethylphenyl)-ethyl amine was prepared from 3-trifluoromethylphenylacetone and 2-aminoethylvinylether according to the method of Example 1. The product was obtained in 32% yield as a colorless oil, b.p. 81°–83°/0.5 mm; $N_D^{25}$ 1.4650.

EXAMPLE 5

N-(2-vinyloxyethyl)-α-methyl-β-(3-trifluoromethylphenyl) Phenethylamine Hydrochloride A solution of 12.4 g. (0.0454 mole) amine in 50 ml. anhydrous ether was treated with 25 ml. of 1.2N ethanol-HCl at ice bath temperature. After cooling overnight at −20°, the product was collected by filtration and washed with anhydrous ether. Obtained 11.2 g. (80%), MP 117° – 118.5°. The salt is soluble in water.

| Elemental Analysis | Calculated | Found |
| --- | --- | --- |
| C | 54.29 | 54.17 |
| H | 6.18 | 6.27 |
| N | 4.52 | 4.54 |

EXAMPLE 6–8

The following compounds are prepared according to the method of Example 1:

N-(2-vinyloxyethyl)-α-methyl-β-(2-fluorophenyl)-ethylamine from 2-fluorophenylacetone and 2-aminoethylvinyl ether N-(2-vinyloxyethyl)-α-methyl-β-(3-iodophenyl)-ethylamine from 3-iodophenylacetone and 2-aminoethylvinyl ether N-(2-vinyloxyethyl)-α-methyl-β-(4-bromophenyl)-ethylamine from 4-bromophenylacetone and 2-aminoethylvinyl ether While the compounds of this invention can be administered alone, that is, as the sole component in a filled capsule, it is preferred to formulate the compounds in various dosage forms suitable for oral administration such as tablets, syrups and the like. Such dosage forms are prepared by methods well known in the art and generally include a pharmaceutically acceptable carrier or diluent such as lactose, starch or sucrose along with lubricating agents such as magnesium stearate and flavoring and sweetening agents and the like.

The components of the present invention, particularly the hydrochloride salts of the compounds of formula B in which R is Cl or $CF_3$ have minimum stimulating properties and are considerably less toxic than fenfluramine and considerably more potent as illustrated by the following data.

Acute Toxicity in Rats

As illustrated in Table I, the hydrochloride salts of the compounds of formula B in which R is Cl or $CF_3$ are approximately four times less toxic than fenfluramine.

Table I

| Compound | Reduction of Food Consumption in Rats | |
| --- | --- | --- |
| | Dose, gm/kg, Post os (P.O.) | Mortality Ratio |
| Fenfluramine | 0/6 | |
| | 0.2 | 2/6 |
| | 0.25 | 4/6 |
| | 0.3 | 5/6 |
| Calculated $LD_{50}$: 0.225 gm/kg (0.19–0.26) | | |
| HCl Salt, R=Cl | 0.25 | 0/6 |
| | 0.5 | 1/6 |
| | 1.0 | 3/6 |
| | 1.25 | 4/6 |
| | 1.50 | 5/6 |
| | 2.00 | 6/6 |
| Calculated $LD_{50}$: 0.95 gm/kg (0.658–1.333) | | |
| HCl Salt, R=$CF_3$ | 0.5 | 0/6 |
| | 0.75 | 1/6 |
| | 0.85 | 2/6 |
| | 1.0 | 4/6 |
| | 2.0 | 5/6 |
| Calculated $LD_{50}$: 1.01 gm/kg (0.765–1.333) | | |

Table II records the percent change in average daily consumption of food at various dosage levels upon administration of fenfluramine or the HCl salt of the compounds of formula B in which R is Cl or $CF_3$ as well as the dose in milligrams per killograms necessary to reduce the intake of food by 50% (ED 50). The data illustrates that the compound in which R is Cl is approximately 2.5 times more potent than fenfluramine while the compound in which R is $CF_3$ is almost 1.2 times as potent. In this study, drugs were administered one hour prior to feeding on the fifth day of regular food intake at doses of 5, 10 and 20 milligrams per kilogram, with five rats being dosed at each level and fifteen rats serving as controls.

Table II

| Compound | Dose, mg/kg Post os (P.O.) | % Change From Control Value in Average Daily Consumption of Food |
| --- | --- | --- |
| Fenfluramine | 5 | −18.7 |
| | 10 | −39.3 |
| | 20 | −50.5 |
| Calculated $ED_{50}$: 20.7 mg/kg | | |
| HCl Salt, R=Cl | 5 | −24.5 |
| | 10 | −53.5 |
| | 20 | −87.3 |
| Calculated $ED_{50}$: 7.7 mg/kg | | |
| HCl Salt, R=$CF_3$ | 5 | −22.9 |
| | 10 | −28.3 |
| | 20 | −76.0 |
| Calculated $ED_{50}$: 17.4 mg/kg | | |

| Compound | Summary Calculated $ED_{50}$* | Relative Potency |
| --- | --- | --- |
| Fenfluramine | | |
| R=Cl, HCl Salt | 7.7 | 2.5 |
| R=$CF_3$, HCl Salt | 17.4 | 1.2 |

*$ED_{50}$: dose (mg/kg) necessary to reduce the intake of food by 50%.

The effect of pre-treatment with fenfluramine and the HCl salts of the compounds of formula B in which R is Cl or $CF_3$ on rat serum lipids and glucose induced by olive oil gavage.

It has been reported that treatment of rats with fenfluramine evoked a rapid increase in the concentration of plasma free fatty acids (Bizzi, A. et al.). Despite the increased fatty acid levels, the drug also produced a decrease in plasma triglycerides in fed, but not fasted, animals (Garattini, S. et al.). The triglyceride-lowering effect of fenfluramine has been correlated at least partially, to inhibition of the intestinal absorption of triglycerides (Bizzi, A. et al.). It has been demonstrated that the sharp rise in plasma triglycerides several hours after olive oil gavage was inhibited by prior treatment of rats with fenfluramine.

The present study was designed to compare the effects of fenfluramine, and the HCl salts of the compounds of formula B in which R=Cl and $CF_3$ on serum glucose and lipid parameters in male rats after an olive oil meal.

Methods

Twenty-four male Sprague Dawley rats (200-250 g.) were divided into 8 groups as follows:

| Pretreatment Drug | Dose (mg/kg) | Olive* Oil | Number of Rats |
|---|---|---|---|
| None | — | — | 3 |
| None | — | + | 3 |
| Fenfluramine | 20 | + | 3 |
| R=Cl, HCl Salt | 20 | + | 3 |
| R=$CF_3$, HCl Salt | 20 | + | 3 |

*20 ml/kg by gavage

The animals were not fasted. Where indicated, the rats were pre-treated (intraperitoneally) with the appropriate drug for 2 hours prior to the administration of olive oil. Three hours after olive oil treatment, the animals were anesthetized with ether and blood samples obtained by cardiac puncture of the exposed heart. In each case, total treatment time was 5 hours.

Results

A summary of the serum parameters measured after the 5 hours experimental period is given in Table III. The data show the following:

1. All of the animals receiving olive oil alone or olive oil and drug showed a 2.5–3.3 fold increase in serum free fatty acids when compared to untreated control rats. The elevation in free fatty acids is probably related to both the oil and the drugs.

2. The HCl salts of the compounds of formula B wherein R is Cl or $CF_3$ were comparable to fenfluramine in inhibiting the increase in serum triglycerides induced by olive oil gavage (50–55% of the oil treated group).

3. The rise in serum glycerol levels induced by olive oil was only slightly inhibited by prior treatment with the drugs (16–35%).

4. Serum glucose concentrations remained relatively unchanged in control and treated groups.

5. Under these conditions, olive oil apparently induced a 45% increase in serum cholesterol. This increase was unaffected by fenfluramine pretreatment, but was reduced 14–19% by the HCl salts of the compounds of formula B in which R is Cl or $CF_3$.

Sidman Avoidance Test in the Rat

The compound fenfluramine and the HCl salt compound of formula B in which R is Cl were examined in the Sidman Avoidance test. The date for the fenfluramine studies show all doses to be effective in producing significant results. The administration of fenfluramine produced results indicative of amphetamine-like compounds, the same increase in response rate and accompanying decrease in shock rate. The HCl salt of the compound of formula B in which R is Cl did not affect performance significantly overall, producing only a sharp decrease in shock rate with response rate remaining stable.

Fenfluramine was run as a standard compound for comparative purposes in the study of appetite-suppressing drugs. The effects of drug-induced behavior are evaluated using the technique of Sidman Avoidance (Sidman, M., J. Comp. Physiol. Psychol. 46:253–261, 1953).

Male, Long Evans black-hooded rats (Simonsen Labs) weighing approximately 500 grams are run individually in Lehigh Valley Electronics rodent test chambers. Sessions (day/night) are 7.5 hours and 14 hours in length, respectively. The paradigm consists of two distinct temporal intervals for neither of which is the rat given any exteroceptive cues. The amount of time that elapses between shocks designates the shock-shock interval, is of a predetermined fixed length (10 seconds), and programmed by a recycling timer. When the rat responds by pressing a lever, the shock-shock interval is terminated and the response-shock interval is started. This interval is also of a predetermined fixed length (30 seconds) and programmed by a recycling timer. Both timers never operate simultaneously. The response-shock interval begins anew each time the rat responds on the lever. If the interval should elapse without the rat responding, a Shock (0.5 seconds, 10 mA) is given via the grid floor and the response-shock interval ends and the shock-shock interval begins.

Drug effects are evaluated as a precentage deviation of the rat's behavior from his baseline rate (responses/minute and shocks/minute). These effects are analyzed in 15 minute segments and an overall percentage deviation (response index and shock index) is determined.

Table IV

The results shown in the following table are based on an 8 mg/kg oral dose.
Number of rats: 4
Session length: 7.5 hours

| Compound | Response Rate | Shock Rate |
|---|---|---|
| Fenfluramine | +15 | −50 |
| R=Cl, HCl Salt | + 7 | −55 |

At 8 mg/kg fenfluramine showed amphetamine-like effect on performance while the HCl salt of the compound of formula B in which R is Cl did not signifi- Table III

| Pre-treatment | Olive Oil | Serum Free Fatty Acids μEq/liter | Serum Concentration (mg%) | | | |
|---|---|---|---|---|---|---|
| | | | Triglycerides | Glycerol | Cholesterol | Glucose |
| None | — | 302±13 | 46±3 | 1.3±.20 | 97±6 | 146±10 |
| None | + | 736±55 | 135±36 | 2.5±.20 | 141±4 | 156±7 |
| Fenfluramine | + | 919±61 | 61±1 | 1.6±.10 | 140±3 | 160±9 |
| R=Cl, HCl Salt | + | 780±66 | 62±7 | 1.8±.30 | 116±8 | 159±1 |
| R=$CF_3$, HCl Salt | + | 870±61 | 62±13 | 2.1±.40 | 122±10 | 159±7 | cantly affect behavior except for the parameter of shock rate which was reduced.

Symtomatology Tests in the Mouse

In contrast to fenfluramine and methamphetamine which show stimulant effects at low doses (10–50 mg/kg), only a weak stimulatory effect was observed at high doses (300-1000 mg/kg) for the HCl salt of the compound of formula B in which R is Cl.

I claim:
1. A method of depressing appetite in a mammal comprising administering to said mammal a therapeutically effective amount of a compound of the formula:

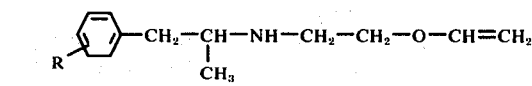

wherein R is hydrogen, halo or trifluoromethyl and acid addition salts thereof.

2. The method of claim 1 which comprises administering N-(2-vinyloxyethyl)-α-methyl-β-(4-chlorophenyl)ethylamine hydrochloride.

3. The method of claim 2 wherein said compound is administered orally in a dosage of from 5 to 20 mg./kg. of body weight daily.

* * * * *